United States Patent [19]

Delevallée et al.

[11] Patent Number: 4,760,070
[45] Date of Patent: Jul. 26, 1988

[54] ANALGESIC COMPOSITIONS AND METHOD

[75] Inventors: Françoise Delevallée, Fontenay-sous-Bois; Roger Deraedt, Pavillons-sous-Bois, both of France

[73] Assignee: Roussel Uclaf, Paris, France

[21] Appl. No.: 930,355

[22] Filed: Nov. 12, 1986

Related U.S. Application Data

[63] Continuation-in-part of Ser. No. 828,399, Feb. 11, 1986, abandoned.

[30] Foreign Application Priority Data

Feb. 14, 1985 [FR] France ................................ 85 02098

[51] Int. Cl.$^4$ ............................................. A61K 31/44
[52] U.S. Cl. ..................................................... 514/282
[58] Field of Search ......................................... 514/282

[56] References Cited

PUBLICATIONS

Chem. Abst., vol. 80—(1974) 103926n.

*Primary Examiner*—Stanley J. Friedman
*Attorney, Agent, or Firm*—Bierman and Muserlian

[57] ABSTRACT

An improved method of treating pain in warm-blooded animals, including humans, by administering a central analgesic and adenine simultaneously or successively at times of a few seconds up to two hours and novel analgesic compositions comprising an analgesically effective amount of a central analgesic and adenine free of side effects.

6 Claims, No Drawings

ANALGESIC COMPOSITIONS AND METHOD

PRIOR APPLICATION

This application is a continuation-in-part of U.S. patent application Ser. No. 828,399 filed Feb. 11, 1986, now abandoned.

STATE OF THE ART

Central analgesics or narcotics are generally considered to possess the same characteristics as morphine in that they cause toxicommania and induce respiratory depression. The synthetic derivatives of morphine most used in therapeutics are pethidine, dextromoramide and pentazocine. The derivatives present the same drawbacks as morphine and research into derivatives possessing the same powerful analgesic effect as morphine but deprived of toxicomanogenic action has to date remain unsuccessful.

One attempt that has been successful is described in U.S. Pat. No. 4,522,816 using a central analgesic and vitamin $B_{12}$ or a derivative thereof. Also pertinent are Chem. Abs., Vol. 89 (1978), p. 442–429 and Vol. 70 (1969), p. 201.

Gourley et al [Proc. Soc. Exp. Bol. Med. 1973, 144(3), p. 774–9] describes treating mice to which adenine was administered with morphine. The adenine was administered at a dose of 50 mg/kg 18 to 19 hours before the administration of morphine and the result was an antagonism to the analgesic activity of morphine.

OBJECTS OF THE INVENTION

It is an object of the invention to provide an improved method of relieving pain in warm-blooded animals with a central analgesic without side effect.

It is another object of the invention to provide improved compositions for relieving pain in warm-blooded animals.

These and other objects and advantages of the invention will become obvious from the following detailed description.

THE INVENTION

The novel method of the invention for relieving pain in warm-blooded animals comprises administering to warm-blooded animals an analgesically effective amount of a central analgesic and adenine simultaneously or successively at times from a few seconds up to two hours, preferably up to one hour. The combined administration of adenine and the central analgesic results in a greater analgesic effect than if the central analgesic is used alone. The amount of adenine used is an analgesically inactive dose.

The treatment method enables a greater analgesic effect to be obtained with a smaller amount of the central analgesic than otherwise necessary and the undesired side effects of the central analgesic are therefore less which is important in human therapy. The preferred central analgesics useful in the method are morphine and synthetic morphine substitutes such as pethidine, pentazocine, dextromoramide and fentanyl which is a very strong morphinic compound.

Examples of the known undesired side effects of morphine-like analgesics at the usual dosages are 1. nausea, vomiting, 2. constipation, 3. respiratory depression, 4. physical and/or psychical habituation in the course of prolonged treatment and 5. state of addition syndromes at the stopping of the treatment, comprising: mydriasis, muscular contractions, pains in the head, sweating, vomiting, diarrhoea, tachycardia, polypnea, hyperthermia, hypertension.

The synergistic analgesic effect obtained as a result of the combined administration is particularly useful in lessening the physical and psychic dependence and the habituation which develops following repeated administrations of analgesics of the morphine-type such as fentanyl, pethidine and pentazocine. The combination of adenine with a morphine analgesic may therefore be referred to as a "morphine economizer".

The increased analgesic effect has been observed with different analgesics such as morphine or a derivative of enkephaline substituted in position 2. From the results of studies, the combination enables, for example, the amount of morphine used to be reduced to one half to one fifth.

The central analgesic and adenine may be administered as a mixture, possibly prepared extemporaneously or can be administered successevely at intervals of a few seconds up to one to two hours. The active ingredients may be administered orally, rectally or parenterally.

The analgesic compositions of the invention are comprised of an analgesically effective amount of central analgesic and adenine and an inert pharmaceutical carrier or excipient. The compositions may be in the form of tablets, dragees, gelules, capsules, granules, suppositories and injectable solutions or suspensions.

Examples of suitable excipients are talc, gum arabic, lactose, starch, magnesium stearate, aqueous or non-aqueous vehicles, fatty substances of animal or vegetable origin, paraffin derivatives, glycols, various wetting, dispersing or emulsifying agents, preservatives.

The relative proportions of the constituents of the combination of the invention are variable and may be for example, from about 1 part of central analgesic to about 0.1 to 50 parts of adenine. The proportions depend greatly on the strength of activity of the central analgesic used, on whether the analgesic chosen is morphine or a more active analgesic than morphine such as pethidine, dextromoramide, fentanyl or less active than morphine such as pentazocinc. The dosages will vary depending on the method of administration, the condition treated and the analgesic used.

The compositions are useful in the treatment of intense pain, particularly pain which is resistant to peripheral antalgic for example, in the course of neoplasia processes, in the treatment of pancreatitis, nephritic or biliary colic and in the treatment of post-operative and post-traumatic pain.

The method of the invention permits the effective amount of the central analgesic to be reduced by one half to one fifth. For example, the usual daily morphine dose of 0.005 to 0.03 g of morphine in the adult can be reduced to 0.001 to 0.01 g when adenine is administered therewith.

In the following examples there are described several preferred embodiments to illustrate the invention. However, it is to be understood that the invention is not intended to be limited to the specific embodiments.

EXAMPLE 1

An injectable solution was prepared containing 5 mg of morphine hydrochloride, 0.5 mg of adenine and sufficient sterile solvent for a final volume of 2 ml.

PHARMACOLOGICAL DATA

A. Increase of analgesic activity of morphine in the rat in the hot plate test

Male rats of an average weight of 110 g were placed individually on a copper plate maintained at 56° C. and reaction to the pain was shown by the licking of a paw or by the animal jumping. The time of this reaction was noted and only those rats which reacted in less than 10 seconds were retained. The rats were divided into homogeneous groups with one group receiving only the vehicle of the administered products. The adenine was administered at a dose of 0.8 mg/kg, inactive by itself, intra-peritoneally, 30 minutes before a dose of 6.5 mg/kg of morphine hydrochloride administered subcutaneously. Under the same conditions of treatment, one group of animals received only adenine and another only morphine hydrochloride and the reactivity of the rats to the pain was noted 30 minutes after the treatment. The results are reported in the following Table.

| Product administered | % Increase in reaction time 30 minutes after the administration of morphine |
|---|---|
| Morphine 6.5 mg/kg S.C. | 92 |
| Adenine + morphine 0.8 mg/kg IP | 280 |

B. Increase of analgesic activity in the mouse of an enkephaline (E) in the hot plate test Adenine administered intra-peritoneally at a dose of 0.8 mg/kg 45 minutes before the intra-cerebroventricular injection of a dose of 0.25 mg/kg of D Ala$^2$-Met$^5$-enkephaline increased the analgesic effect of the latter at 15 minutes. The % increase in reaction time at 15 minutes was 100% for E and 231% for adenine and E.

Various modifications of the compositions and method of the invention may be made without departing from the spirit or scope thereof and it should be understood that the invention is intended to be limited only as defined in the appended claims.

What is claimed is:

1. A method of relieving pain in warm-blooded animals comprising administering to warm-blooded animals an analgesically effective amount of a central analgesic and sufficient adenine to potentialize the central analgesic simultaneously or successively at times from a few seconds up to two hours, the central analgesic; adenine ratio being 1 part by weight to 0.1 to 50 parts parts by weight.

2. The method of claim 1 wherein the central analgesic is selected from the group consisting of morphine, pethidine, fentanyl, pentazocine and dextromoramide.

3. The method of claim 1 wherein the central analgesic is morphine.

4. The method of claim 1 wherein the central analgesic and adenine are separately administered.

5. The method of claim 1 wherein the central analgesic and adenine are administered simultaneously.

6. The method of claim 1 wherein the central analgesic is a derivative of enkephaline substituted in the 2-position.

* * * * *